United States Patent [19]

Shapiro

[11] Patent Number: 4,495,948
[45] Date of Patent: Jan. 29, 1985

[54] TRACHEAL TUBES

[75] Inventor: Seymour W. Shapiro, Lowell, Ind.

[73] Assignee: Bivona Surgical Instruments, Inc., Gary, Ind.

[21] Appl. No.: 291,322

[22] Filed: Aug. 10, 1981

[51] Int. Cl.³ ............................................. A61M 16/00
[52] U.S. Cl. .................................. 128/207.15; 604/99
[58] Field of Search ....................... 128/200.26, 203.12, 128/207.14, 207.15, 348, 349 B, 349 BV, 207.16; 604/96, 99

[56] References Cited

U.S. PATENT DOCUMENTS

| | | | |
|---|---|---|---|
| 3,504,676 | 4/1968 | Lomholt | 128/207.15 |
| 3,640,282 | 2/1972 | Kamen et al. | 128/207.15 |
| 4,020,849 | 5/1977 | Jackson | 128/207.15 |
| 4,285,340 | 8/1981 | Gezari et al. | 128/207.15 |

Primary Examiner—Henry J. Recla
Assistant Examiner—Karin M. Reichle
Attorney, Agent, or Firm—Emrich & Dithmar

[57] ABSTRACT

A tracheal tube for use in intubation of a trachea, and embodying a resilient yieldable cuff for effecting a seal between the tube and the trachea. The cuff contains a resilient member, which normally resiliently maintains the cuff in an expanded position away from the tube. The tube also embodies a secondary tube mounted on the tracheal tube in communication with the interior of the cuff for applying a vacuum to the cuff for contracting the latter. The tracheal tube also embodies a connector in communication with the interior thereof for connecting the secondary tube to the interior of the tracheal tube during mechanical ventilation and thereby increasing and decreasing the pressure within the cuff in accordance with the pressure variation in the tracheal tube during such an operation.

9 Claims, 6 Drawing Figures

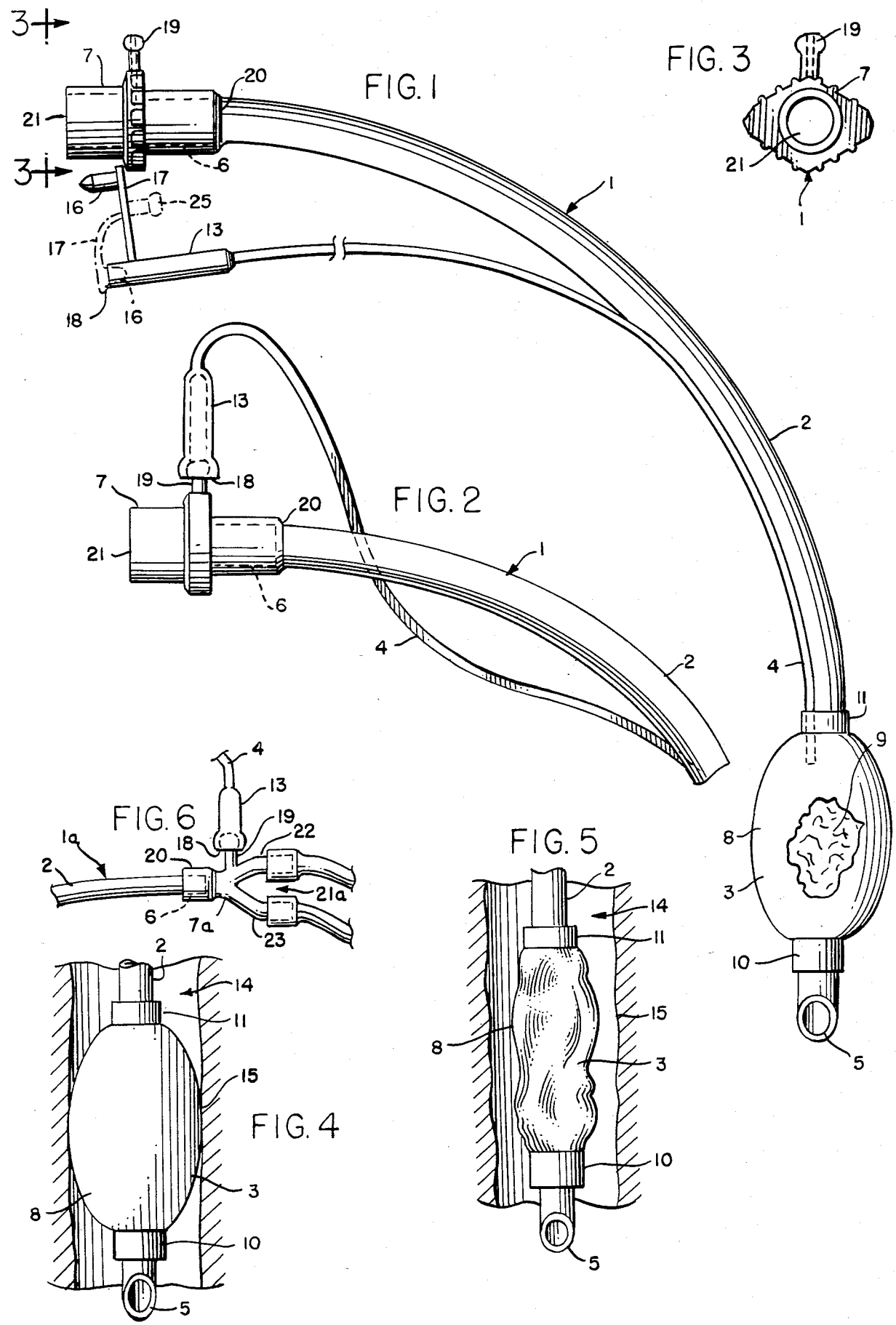

TRACHEAL TUBES

BACKGROUND OF THE INVENTION

The present invention relates to tracheal tubes and, more particularly, to tracheal tubes of the type embodying a cuff for effecting a seal between the tube and a trachea.

The primary object of the present invention is to afford a novel tracheal tube.

Another object is to enable an effective seal between a tracheal tube and a trachea to be effected in a novel and expeditious manner.

A further object of the present invention is to afford a novel tracheal tube which is particularly useful during high positive pressure ventilation of a respiratory tract.

Tracheal tubes, as that term is used herein, may be of different types, such as, for example, orotracheal tubes, nasotracheal tubes and tracheostomy tubes. Also, such tubes may be flexible, the main body portion thereof being made of flexible material such as, for example, rubber or a suitable plastic material such as, for example, polyvinylchloride, or the like, or they may be stiff or rigid, being made of material such as stainless steel, or the like, the latter type of tubes being primarily useful as tracheostomy tubes. The present invention is intended for use in the construction of all such tracheal tubes.

As is well known in the art, tracheal tubes are commonly inserted into a person's trachea for various purposes, such as, for example, to enable the person to breathe, or to enable intermittent positive pressure ventilation of the respiratory tract to be carried out. An important object of the present invention is to afford a novel tracheal tube which is particularly well adapted for the latter aforementioned use, especially where high ventilating pressures are utilized.

Often, it is highly important, particularly in such instances as when positive pressure ventilation of the respiratory tract is to be carried out, that an airtight or substantially airtight seal be provided between the tracheal tube and the trachea. Heretofore, various attempts have been made to effect such seals between tracheal tubes and the trachea, such as, for example, by using large tubes which completely fill the trachea, or using cuffs on the tubes, which are expandable outwardly into engagement with the inner wall of the trachea.

Cuffed tracheal tubes heretofore known in the art, have been of two types. In one of those types, cuffs in the form of elastic diaphragms or tubes, made of elastic material, such as, for example, latex rubber, have been mounted on the main tube in sealed surrounding relation thereto, with the cuff normally, and when being inserted into the trachea, being in uninflated or deflated condition. With such devices, after the intubation device has been inserted into the trachea, the cuff is inflated like a balloon, by feeding air or other working fluid thereinto at a positive pressure to thereby expand the cuff into engagement with the inner wall of the trachea. However, it has been found that such devices have several inherent disadvantages, the primary disadvantage being that they commonly cause injury to the trachea, causing lesions such as tracheal stenosis, tracheal malacia and localized erosion, and the like, particularly if it is necessary for the tube to remain in the trachea for prolonged periods of time.

The other type of cuffed tracheal tubes heretofore known in the art is of a type such as that shown in U.S. Pat. No. 3,640,282, issued to Jack M. Kamen and Carolyn J. Wilkinson, on Feb. 8, 1972, wherein the cuff embodies a cover filled with resilient material, with the cuff normally being disposed in expanded position and being collapsed by applying a vacuum thereto during insertion of removal of the tube into or from the trachea, respectively. It is with respect to this latter type of tracheal tube to which the present invention pertains.

Current techniques of mechanical ventilation of the respiratory tract often employ relatively high positive air pressure. This pressure is highest at the peak of the inspiratory phase and lowest at the termination of the expiratory phase.

The human trachea is elastic. The degree of elasticity varies and is dependent upon a number of factors, the majority of which cannot or should not be controlled during such mechanical ventilation.

The two aforementioned factors, namely, current mechanical ventilation techniques and tracheal elasticity create a problem for cuffed endotrachael tubes to overcome. If the cuff is of the aforementioned air-filled type, the volume of air required to "no leak" ventilation at peak inspiratory airway pressure exceeds the volume of air needed in the cuff during expiration. The result in many instances is a progressive stretching of the trachea with ultimate tracheal injury.

On the other hand, when the cuff on the tracheal tube is of the expandable-material filled type, such as, for example, th type disclosed in the aforementioned Kamen and Wilkinson U.S. Pat. No. 3,640,282, the cuff contents exert prgressively less force against the tracheal wall as the elastic trachea's volume is expanded at peak inspiratory pressure. If this expansion of the elastic trachea is of sufficient magnitude, the result may be an inadequate seal between the cuff and the trachea. It is an important object of the present invention to enable this danger to be overcome in a novel and expeditious manner.

Heretofore, in an attempt to insure the proper seal between the trachea and a cuffed tracheal tube during mechanical ventilation and to minimize or prevent tracheal injury, cuff inflator machines have been used. These machines either attempt to vary the cuff volume and pressure synchronously with a companion ventilating machine or to maintain a constant cuff pressure while varying the cuff volume during the changing requirements of a complete inspiration/expiration cycle. These machines have several disadvantages, among which are that they are expensive and are subject to the maintenance and calibration problems inherent to precise machinery. It is an important object of the present invention to enable the aforementioned seal-maintenance problem to be overcome in an inexpensive, novel and expeditious manner.

Another object of the present invention is to afford a novel tracheal tube of the aforementioned normally-expanded type, wherein the pressure of the cuff against the tracheal wall, and the cuff volume during mechanical ventilation of a respiratory tract, may be controlled in a novel and expeditious manner.

Another object of the present invention is to afford a novel tracheal tube which is practical and efficient in operation, and which may be readily and economically produced commercially.

A still further object of the present invention is that the method prevents the peak pressure in the cuff from exceeding peak airway pressure.

Other and further objects of the present invention will be apparent from the following description and claims and are illustrated in the accompanying drawings which, by way of illustration, show a preferred embodiment of the present invention and the principles thereof and what I now consider to be the best mode in which I have contemplated applying these principles. Other embodiments of the invention embodying the same or equivalent principles may be used and structural changes may be made as desired by those skilled in the art without departing from the present invention and the purview of the appended claims.

DESCRIPTION OF THE DRAWINGS

In the drawings:

FIG. 1 is a side elevational view of a tracheal tube embodying the principles of the present invention;

FIG. 2 is a fragmentary, side elevational view of a portion of the tracheal tube shown in FIG. 1, showing parts thereof disposed in different operative position;

FIG. 3 is an end elevational view of the tracheal tube shown in FIG. 1, looking in the direction of the arrows 3—3 in FIG. 1;

FIG. 4 is a fragmentary elevational view of the tracheal tube shown in FIG. 1, showing the cuff disposed in a trachea in expanded position, the trachea being shown diagrammatically;

FIG. 5 is a view similar to FIG. 4, showing the cuff in uninflated or deflated condition; and FIG. 6 is a fragmentary view of a tracheal tube of the type shown in FIG. 1, illustrating a modified form of the present invention.

DESCRIPTION OF THE EMBODIMENTS SHOWN HEREIN

A tracheal tube or intubation device 1, embodying the principles of the present invention, is shown in the drawings to illustrate the presently preferred embodiment of the present invention.

The tracheal tube 1, like the tracheal tube shown in the aforementioned Kamen and Wilkinson U.S. Pat. No. 3,640,282, embodies, in general, an elongated tube 2 having a cuff 3 mounted on one end portion thereof, with a tube 4 extending into the cuff 3 for a purpose which will be described in greater detail presently. The tube 2 may be of any suitable construction and is for the purpose of feeding air, or the like, into and out of the respiratory tract of a patient into whose trachea the tracheal tube or intubation device 1 has been inserted. Commonly, when the tracheal tube 1 is to be used as an endotracheal tube, such as either an orotracheal or nasotracheal tube, the tube thereof is peferably flexible and may be made of any suitable material such as, for example, rubber of a suitable plastic, such as polyvinylchloride, or the like. However, in other instances, such as, for example, when the tracheal tube 1 is to be used as a tracheostomy tube, it may be desired to have the tube 2 thereof be rigid in construction and made of suitable material such as, for example, stainless steel, or the like.

In the drawings, the tube 2 is shown as having a distal end 5 for insertion into a trachea, and a proximal end 6 on which a connector 7 is mounted for connecting the tube 1 to a suitable source of oxygen, or the like, or, when mechanical ventilation of a respiratory tract is to be carried out, to a ventilating machine, or the like. It will be understood by those skilled in the art that the tube 2 may be of any suitable length, such tubes commonly being in the nature of nine to fourteen inches in length, when used as an endotracheal tube, and commonly being considerably shorter when used as a tracheostomy tube.

Like the cuff shown in the aforementioned Kamen and Wilkinson U.S. Pat. No. 3,640,282, the cuff 3 includes an air impervious cover 8 and a body portion 9 disposed within the cover 8, FIG. 1. Both the body portion 9 and the cover 8 are disposed around a portion of the tube 2 in spaced relation to the ends 5 and 6 thereof. In practice, the cuff 3 will normally be disposed substantially closer to the end 5 of the tube 2 than to the end 6 thereof, such as, for example, being spaced from the end portion 5 a distance in the nature of one-half to three-fourths of an inch on a tube having an overall length of fourteen inches. However, as will be appreciated by those skilled in the art, the cuff 3 may be disposed at any suitable location along the tube 2, the particular location thereof depending upon the intended use of the intubation device 1. For example, normally, when end 5 of the tube 2 is to be inserted into the windpipe or trachea only, the cuff 3 preferably will normally be spaced a relatively short distance from the end 5, such as, for example, the aforementioned one-half to three-fourths of an inch. However, if the intubation device 1 is to be inserted further than into the trachea, such as, for example, into the bronchia, the cuff 3 preferably would be spaced a greater distance from the end 5 so that it would remain in the trachea when the end 5 was inserted into the bronchia.

The cover 8 is flexible and may be made of any suitable material such as, for example, latex rubber or a suitable plastic sheet material, such as, polyvinylchloride, or the like. Preferably, it also is elastic for reasons which will be discussed in greater detail presently, and, of course, under such circumstances it would be made of a suitable elastic material such as the aforementioned latex or silicone rubber.

The cover 8 is tubular in form, and the end portions 10 and 11 thereof are hermetically sealed to the outer surface of the tube 2 by suitable means, such as, for example, being vulcanized thereto or by a suitable cement such as rubber cement, or the like.

The body portion 9 affords a resilient mass which preferably completely fills the cover 8 between the end portions 10 and 11 thereof and, when the intubation device 1 is disposed in normal inoperative position outside the trachea, preferably is effective to yieldingly hold the cover 8 in fully expanded position, as shown in FIG. 1. The body portion 9 may be made of a spongelike resilient material having a multitude of interstices spread therethrough, such as, for example, sponge rubber or a suitable resilient plastic material, such as, for example, foamed polyurethane, or the like.

The tube 4 has one end portion 12 extending into the cuff 3, FIG. 1. As shown in the drawings, the tube 4 extends along the tube 2 and, preferably, the tube 4 is formed integrally with the tube 2 and terminates in a free end portion 13 which projects outwardly from the end 6 of the tube 2. However, as will be appreciated by those skilled in the art, the tube 4 may be formed separately from the tube 2 and inserted into the cuff 3 in a suitable manner without departing from the purview of the broader aspects of the present invention.

In the intubation device 1 shown in the drawings, wherein the tube 4 extends along the tube 2, FIG. 1, the tube 4 extends through the end portion 11 of the cover 8 and the latter is hermetically sealed thereto in the same manner as it is so sealed to the tube 2. With this construction, it will be seen that when the tube 4 is open to the atmosphere at the end portion 13 thereof, and the intubation device 1 is disposed outside of a trachea, the body portion 9 is effective to yieldingly hold the cover 8 in fully outwardly extended position, as shown in FIG. 1. However, by the application of a vacuum to the end portion 13 of the tube 4, air may be withdrawn from within the cover 8 through the tube 4 to thereby afford a partial vacuum within the cuff 3 and cause it to collapse from the position shown in FIG. 1 to a position such as that shown in FIG. 5, because of the imbalance between the pressures within the cover 8 and the atmospheric pressure exteriorly thereof. It will be remembered that, preferably, the body portion 9 is made of a resilient material having interstices therein, such as, for example, the aforementioned foam rubber or foamed polyurethane. With such construction, the withdrawal of air from within the cover 8 may be substantially uniform throughout the entire area between the end portions 10 and 11 thereof, so as to effect a relatively uniform substantially complete collapse of all portions of the cover 8 throughout the length thereof, as illustrated in FIG. 5.

As is true with respect to the tracheal tube shown in the aforementioned Kamen and Wilkinson U.S. Pat. No. 3,640,282, with the intubation device 1 constructed in the aforementioned manner, when it is desired to insert it into a trachea such as the trachea 14 diagrammatically shown in FIGS. 4 and 5, a partial vacuum may be applied to the end portion 13 of the tube 4 to thereby cause the cuff 3 to move from its normal expanded position shown in FIG. 1 to a collapsed position such as that shown in FIG. 5. While maintaining the vacuum on the tube 4, the tracheal tube 1 may be inserted into a trachea, such as the trachea 14, the cuff 3 being disposed in the aforementioned collapsed position to thereby facilitate such an insertion. Thereafter, when the tracheal tube 1 has been inserted into the desired position in the trachea 14, the vacuum of the tube 4 may be released to thereby permit the cover 8 to be expanded outwardly by the yielding expansion of the resilient body member 9, the expansion of the cover 8 from the collapsed position being to a position wherein it is yieldingly held by the body portion 9 in engagement with the inner wall 15 of the trachea 14, FIG. 4. Such expansion is caused by the resiliency of the body portion 9 and is a direct result of the volumetric expansion thereof. This is to be distinguished from the expansion of the aforementioned cuffs heretofore known in the art, which cuffs are expanded by the application of a positive pressure by the introduction of air or other working fluid thereinto under pressure.

In the preferred form of intubation device 1 shown in the drawings, a plug 16 is secured to the end portion 13 of the tube 4 by a flexible strap 17, FIG. 1. The plug 16 is of such size that it may be manually inserted into and removed from the free end 18 of the end portion 13 of the tube 4. With this construction, after a partial vacuum has been applied to the cuff 3 to thereby move it into the aforementioned collapsed position, such as shown in FIG. 5, the plug 16 may be manually moved from its normal withdrawn position, shown in solid lines in FIG. 1, to its inserted position shown in broken lines therein to thereby close the end 18 of the end portion 13 of the tube 4 and thereby retain the vacuum in the cuff 3 during manipulation of the tracheal tube 1. After the tracheal tube 1 has been disposed in the desired position within a trachea, the plug 16 may be manually withdrawn from the end 18 of the end portion 13 of the tube 4 to thereby open the tube 4 to the atmosphere and permit the cuff 3 to move from its collapsed position, such as shown in FIG. 5, to an expanded position, such as shown in FIG. 4. As will be appreciated by those skilled in the art, the plug 16 is shown herein merely to illustrate the preferred form of the intubation device 1, and other means of closing the tube 4, such as, for example, squeezing the end portion 13 thereof may be used without departing from the purview of the present invention.

It will be remembered that the cuff 3 may be made of any suitable flexible material, but that preferably it is made of an elastic material, such as, for example, latex or silicone rubber. The latter is true because with the cover made of a suitable elastic material it may be so constructed that no sharp wrinkles are formed therein in any position thereof between the fully expanded position shown in FIG. 1 and the collapsed position shown in FIG. 5, whereas, with some materials which are flexible but do not have this degree of elasticity such as, for example, certain plastic sheet materials, and the like, sharp wrinkles are formed when the cover 8 is disposed in a position wherein it has extended outwardly less than that which it occupies when fully extended. It is important that the cover 8 is wrinkled without producing sharp edges when the cuff 3 is in fully collapsed position, as shown in FIG. 5, and it is equally important that no sharp wrinkles be formed in the cover 8 when the cuff 3 is disposed in operative engagement with a trachea, such as is shown in FIG. 4. Therefore, to insure against such sharp wrinkles, I prefer that the cover 8 be made of a suitable elastic material, such as, for example, the aforementioned latex or silicone rubber.

When the tracheal tube 1 is inserted in the trachea of a patient for the purpose of permitting the patient to breathe therethrough, and, particularly when the tube 1 is to remain in the patient for a prolonged period of time, it is desirable that the cuff 3 not exert an excessive pressure against the inner wall 15 of the trachea 14 so as to protect against injury to the trachea 14, as is recognized in the aforementioned Kamen and Wilkinson U.S. Pat. No. 3,640,282. However, such minimal outward pressure of the cuff 3 against such a trachea, while highly effective in affording a seal with the trachea when the patient is merely breathing therethrough, or the like, such pressure in some instances, may not be effective to afford a proper or desired seal with the trachea under the high ventilating pressure often used in the mechanical ventilation of a respiratory tract. A main purpose of the present invention is to afford a novel tracheal tube which, while retaining the highly desirable characteristics of a tracheal tube such as that shown in the aforementioned Kamen and Wilkinson U.S. Pat. No. 3,640,282, for many purposes, such as, for example, when the tracheal tube is merely being used by a patient for breathing therethrough, the sealing pressure of the cuff 3 against such a trachea, such as the trachea 14, may be increased in a novel and expeditious manner, during certain operations, such as, for example, the mechanical ventilation of the respiratory tract of a patient in which high ventilating pressures are utilized, so as to insure the desired, effective seal between the intubation device and the trachea and to insure that the peak cuff pressure does not exceed the peak airway or ventilating pressure.

For this purpose, my novel tracheal tube 1 embodies a tubular coupling 19 projecting laterally outwardly from the tube 2 and in communication with the interior of the latter. In the preferred form of tracheal tube 1, shown in FIGS. 1–5, the coupling 19 is embodied in the connector 7, as an integral part thereof. The connector 7 has one end portion 20 connected to the proximal end portion 6 of the tube 2 and another end portion 21 projecting outwardly therefrom for connection to a source of oxygen, or the like, or to mechanical ventilation equipment, or the like, as is well known in the art. The coupling 19 is disposed between the end portions 20 and 21, of the connector 7, and in the preferred form of the invention shown in the drawings, projects radially outwardly therefrom.

With this construction, when the intubation device 1 is connected through the connector 7 to a ventilating machine, the end 18 of the end portion 13 of the tube 4 may be mounted on, and thereby connected to the coupling member 19, as shown in FIG. 2. With the end portion 13 of the tube 4 so connected to the coupling 19, the pressure in the cuff 3 will parallel the ventilating or airway pressure in the tube 2 and the trachea 14, thus permitting the volume of the compliant cuff 3 to vary with the volume of the trachea 14, to thereby maintain an effective seal between the cuff 3 and the inner wall 15 of the trachea 14 even when the trachea 14 has been expanded, such as, for example, at peak inspiratory pressure within the trachea. When the tracheal tube 1 is not being used in procedures in which high ventilating pressures are utilized, the end portion 13 of the tube 4 may be disconnected from the coupling 19 and closed, such as for example, by an attachment cup 25 shown in dotted lines in FIG. 1, to thereby return the tracheal tube 1 to a form corresponding to that of the tracheal tube shown in the aforementioned Kamen and Wilkinson U.S. Pat. No. 3,640,282.

Normally, during mechanical ventilation, gases having a relative humidity of one hundred percent are delivered to the lungs. In many, if not all instances, moisture in the cuff 3 is undesirable. To protect against this, if desired, a moisture absorbing cartridge, not shown, may be interspersed between the end portion 21 of the connector 7 and the coupling 19. This cartridge may be of any suitable type readily available on the market, but preferably should be of the type that changes color when it becomes moisture laden so as to alert those in attendance that a replacement cartridge is needed.

As will be appreciated by those skilled in the art, the coupling 19 is shown herein as a part of the connector 7 merely by way of illustrating the presently preferred form of the present invention and not by way of limitation, and the coupling 19 may be connected to the tracheal tube 1 in other manners, such as, for example, directly to the tube 2, as an integral portion thereof, without departing from the purview of the broader aspects of the present invention.

In FIG. 6, a modified form of the present invention is shown, and parts which are the same parts shown in FIGS. 1–5 are indicated by the same reference numerals, and parts which are similar to, but have been substituted for parts shown in FIGS. 1–5 are shown by the same reference numerals with the suffix "a" added thereto.

The tracheal tube 1a shown in FIG. 6 is of the same construction as the tracheal tube 1 shown in FIGS. 1–5 except that a modified form of connector 7a has been substituted for the connector 7.

Like the connector 7, the connector 7a has an end portion 20 mounted on the end portion 6 of the tube 2 of the tracheal tube 1a. However, unlike the connector 7, the end portion 21a of the connector 7a is not of one-piece construction but embodies two branches 22 and 23 by which the tube 1a may be connected to two separate things, such as, for example, a source of air and a source of oxygen, or a source of air and a ventilating machine, or the like.

Otherwise, the construction and operation of the tracheal tube 1a is the same as that of the tracheal tube 1, the coupling 19 being disposed between the end portions 20 and 21a of the coupling 7a for connection to the end 18 of the end portion 13 of the tube 4, as shown in FIG. 6.

From the foregoing, it will be seen that the present invention affords a novel and practical tracheal tube.

In addition, it will be seen that the present invention affords a novel and practical tracheal tube which is particularly well adapted for use in the mechanical ventilation of the respiratory tract of a patient.

Also, it will be seen that the present invention affords a novel tracheal tube of the aforementioned type, which is practical and efficient in operation and which may be readily and economically produced commercially.

Thus, while I have illustrated and described the preferred embodiments of my invention, it is to be understood that these are capable of variation and modification, and I therefore do not wish to be limited to the precise details set forth but desire to avail myself of such changes and alterations as fall within the purview of the following claims.

I claim:

1. A tracheal tube comprising
   a. a first elongated tube having an outer surface, a proximal end and a distal end,
   b. a cuff mounted on said first elongated tube adjacent to said distal end and in spaced relation to said proximal end,
   c. said cuff comprising
      (1) a flexible tubular cover
         (a) disposed on said first elongated tube in surrounding relation thereto, and
         (b) having its ends secured to said outer surface, and
      (2) a resilient body portion mounted in said cover,
   d. said body portion having
      (1) normally an expanded position wherein it is effective to hold a portion of said cover outwardly away from said first elongated tube, and
      (2) a collapsed position wherein the outer surface thereof is disposed closer to said first elongated tube than in said expanded position to thereby permit said portion of said cover to assume a position closer to said first elongated tube,
   e. means for delivering positive and negative pressures, respectively, to the interior of said cover whereby when a negative pressure is delivered, said body portion moves toward said collapsed position and when said negative pressure is removed, said body portion moves toward said expanded position, said delivery means having first connection means adapted to be connected to positive and negative pressures, respectively, and
   f. second connection means having one end fluidically connected directly to the interior of said first elongated tube and an opposite end adapted to be connected to said first connection means and whereby said first connection means is first connected to a negative pressure to collapse said body portion to permit insertion of said tracheal tube into a trachea, disconnected to permit expansion of said body portion within said trachea and subsequently connected to said second connection means to communicate the pressure in the interior of said first elongated tube to the interior of said cover.

2. A tracheal tube as defined in claim 1, and in which
   a. means for delivery comprises a second elongated tube having a proximal end and a distal end,
   b. said distal end of said second elongated tube is disposed in said cover,
   c. said proximal end of said second elongated tube comprising said first connection means, and
   d. said second connection means comprises a tubular member projecting radially outwardly from said proximal end of said first elongated tube and positioned to receive said first connection means thereon.

3. A tracheal tube as defined in claim 2, and which includes
   a. means for opening and closing said proximal end of said second tube.

4. A tracheal tube as defined in claim 3, and in which
   a. said opening and closing means comprises a plug secured to said second elongated tube and adapted for insertion into and withdrawal from said proximal end thereof.

5. A tracheal tube as defined in claim 2, and in which
   a. said body portion comprises a spongelike elastic mass having interstices therethrough.

6. A tracheal tube as defined in claim 5, and in which
   a. said mass comprises sponge rubber.

7. A tracheal tube for intubating a trachea and comprising
   a. a first elongated tube means adapted for insertion into a trachea and having an outer surface, a proximal end and a distal end,
   b. a resilient cuff mounted on said first elongated tube means adjacent to said distal end and in spaced relation to said proximal end thereof,
   c. said resilient cuff including resilient means mounted therein for yieldingly holding said cuff outwardly away from said first elongated tube means,
   d. said resilient cuff having
      (1) a normal position wherein said resilient means is effective to hold a portion of said cuff radially outward from said first elongated tube means, and
      (2) another position wherein the resilient means yields to thereby permit said portion of said cuff to extend a lesser radial distance from said first elongated tube means in said normal position,
   e. means connected to said cuff for delivering positive and negative pressures, respectively, to the interior of said cuff whereby, when a negative pressure is delivered, said resilient cuff moves toward said other position and when said negative pressure is removed, said resilient cuff moves toward said normal position, said delivery means having a first connection means adapted to the be connected to positive and negative pressures, respectively, and
   f. second connection means having one end fluidically connected directly to the interior of said first elongated tube means and an opposite end adapted to be connected to said first connection means and whereby during intubation of said trachea under positive ventilating pressure said first connection means is first connected to a negative pressure to move said cuff towards said other position to permit insertion of said tracheal tube into said trachea, disconnected to permit expansion of said cuff within said trachea and subsequently connected to said second connection means to communicate the pressure in the interior of said first elongated tube means to the interior of said cuff for increasing the volume of said cuff in accordance with the increase in tracheal pressure caused by said positive ventilating pressure and thereby, the increase in tracheal volume, to provide that the peak cuff pressure is equal to the peak ventilating pressure.

8. A tracheal tube as defined in claim 7, and in which
   a. said means for delivery comprises a second elongated tube means having a proximal end and a distal end,
   b. said distal end of said second elongated tube means is disposed with said cuff,
   c. said proximal end of said second elongated tube means comprising said first connection means, and
   d. said second connection means comprises a tubular member projecting radially outwardly from said proximal end of said first elongated tube means and positioned to receive said first connection means thereon.

9. A tracheal tube as defined in claim 8, and in which
   a. said resilient cuff includes a resilient, rubber, tubular cover
      (1) disposed on a portion of said distal end portion of said first elongated tube means in surrounding relation thereto, and
      (2) having opposite end portions sealingly secured to the outer surface of said first elongated tube means and
   b. said resilient means comprises a sponge rubber mass.

* * * * *

UNITED STATES PATENT AND TRADEMARK OFFICE
CERTIFICATE OF CORRECTION

PATENT NO. : 4,495,948
DATED : January 29, 1985
INVENTOR(S) : Seymour W. Shapiro It is certified that error appears in the above—identified patent and that said Letters Patent is hereby corrected as shown below:

Column 2, line 31, delete "th", insert --the--;

Column 10, line 2, after "means" insert --than--;

Column 10, line 10, delete "the";

Column 10, line 36, delete "with", insert --within--.

Signed and Sealed this

Twentieth Day of August 1985

[SEAL]

Attest:

DONALD J. QUIGG

Attesting Officer    Acting Commissioner of Patents and Trademarks